United States Patent [19]

Gerber

[11] 4,022,793

[45] May 10, 1977

[54] TRIAMINO PYRIDINE COMPOUNDS

[75] Inventor: Arthur H. Gerber, University Heights, Ohio

[73] Assignee: Horizons Research Incorporated, Cleveland, Ohio

[22] Filed: Aug. 18, 1975

[21] Appl. No.: 605,484

Related U.S. Application Data

[62] Division of Ser. No. 438,392, Jan. 31, 1974, abandoned.

[52] U.S. Cl. .......................... 260/294.8 F; 424/263
[51] Int. Cl.² ......................................... C07D 213/74
[58] Field of Search ............... 260/296 R, 294.8 F, 260/294.9, 240 R, 295 AM, 295 R

[56] References Cited

UNITED STATES PATENTS

| | | | |
|---|---|---|---|
| 3,634,439 | 1/1972 | Ayad | 260/295 AM |
| 3,740,410 | 6/1973 | Gerber | 260/295 AM |
| 3,838,154 | 9/1974 | Gerber | 260/294.8 F |

OTHER PUBLICATIONS

Koenigs et al., Ber. Deut. Chem., vol. 57, pp. 1179 to 1187 (1924).
Tschitschibabin et al, Ber. Deut. Chem. vol. 61, pp. 1223 to 1235.
Petrow et al., J. Chem. Soc., 1946, pp. 588 to 591.
Houben–Weil, Methoden der Organischen Chemie, 4th Ed., Band XI/1, pp. 248 to 253, Georg. Thieme Verlag, Stuttgart, Germany (1957).
Tomasik et al., Roczniki Chemi, vol. 40, pp. 637 to 642 (1966).

*Primary Examiner*—John D. Randolph
*Attorney, Agent, or Firm*—Lawrence I. Field

[57] ABSTRACT

Triamino pyridine compounds, and their precursors, are described from which polymers exhibiting excellent thermal stability are prepared by reaction with selected di-, tri- or tetra-functional acid derivatives.

3 Claims, No Drawings

TRIAMINO PYRIDINE COMPOUNDS

This application is a division of application Ser. No. 438,392 filed Jan. 31, 1974, and now abandoned.

This invention relates to triamino pyridine compounds and methods for the preparation of said compounds, and to the poly(amide-benzimidazoles), poly(imide-imidazopyrrolones), poly(imidebenzimidazoles), and poly(amide-imidazopyrrolones) derived from said triamino pyridine compounds and to their preparation. These polymers are thermally stable and can be processed in many useful forms for high temperature applications such as in films, coatings, fibers, adhesive and laminating formulations, as matrices for structural composites, and semi-permeable membranes.

Polymers produced from the heterocyclic triamines of this invention differ markedly from polymers produced from known carbocyclic triamines such as 1,2,4-triaminobenzene. and 3,4,4′triaminobiphenyl. These carbocyclic triamines or their acid salts reportedly produce gelled polymer upon reaction with bis(acid halides), and 1,2,3-triaminobenzene, unlike its 1,2,4-isomer, is not known to yield soluble high molecular weight polymers from dianhydrides.

The 2,3,5- and 3,4,5-triaminopyridines and hydrochloride salts thereof are known [Roczniki Chem., 40 (4), 637 (1966), J. Heterocyclic Chem., 7 (5), 1195 (1970)] and are related to some of the monomers of this invention. The novel mono- or di- ring alkylated homologs of these triaminopyridines exhibit the following advantages as compared with the previously known compounds. They are (1) more soluble as their acid salts, the use of which permits a faster polymerization; (2) the resulting polymers are more soluble and easier to process; and (3) the presence of not more than one vulnerable ring C-H bond in the residual triamine nucleus of cyclized polymer leads to improved thermal stability.

Triamino pyridines and picolines where the $-NH_2$ groups are located 4,5,6- or 2,3,6-, 2,3,4-, or 2,4,6- are known, but these triamines are unsatisfactory for practicing the polymerization process herein described.

One object of this invention is to provide monomers which contain functionally reactive groups other than $-NH_2$ or $-NH-$ groups for the preparation of polymers which can be easily crosslinked.

Another object is to provide dinitro intermediates of the triamines and methods for their preparation.

A further object of the invention is to provide polymers of enhanced thermal stability by reaction of such triamino compounds with suitable bis(acid halides) and other acid derivatives.

Other objects will become apparent or will be pointed out in the description which follows of preferred embodiments of the invention.

The triamino compounds of this invention are represented by the following formula:

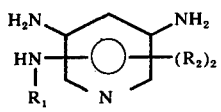

Formula I wherein each $R_2$ represents a monovalent member selected from the group consisting of hydrogen, methyl, ethyl, propyl, butyl and pentyl, and both $R_2$'s are not required to be the same; and $R_1$ is a monovalent member selected from the group consisting of hydrogen, alkyl, substituted alkyl, alkenyl, substituted alkenyl, arylalkyl, aryl, heteroaryl, heteroarylalkyl, substituted arylakyl, substituted aryl and substituted heteroaryl, with aryl and heteroaryl including monocyclic, linear bicyclic and fused ring structures, typical substituents within the scope of this invention include: methyl, phenyl, pyridyl, F (aromatic), Cl (aromatic), $-CN$, $-COOH$ and its salts, $-COOC_6H_5$, $-SO_3H$ and its salts, $-SH$, thioaryl, thioalkyl, $-CH=CHC_6H_5$, and N,N-(dialkylamino), with the proviso that not all $R_2$'s and $R_1$'s are equal to hydrogen.

Suitable $R_1$'s include the following which are intended to be illustrative of the manner in which $R_1$ may vary: methyl, ethyl, propyl, butyl, pentyl, allyl, crotyl, phenyl, biphenyl, pyridyl, quinolyl, N,N-(dialkylamino)alkyl, $-C_6H_4COOH$ and salts thereof, $-C_6H_4SO_3H$ and salts thereof;

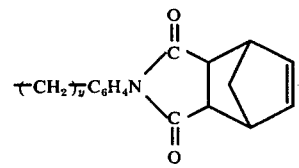

wherein y is 0, 1 or 2.

Representative specific triamino pyridine compounds of the present invention include the following:
3,5-diamino-2-benzylaminopyridine
3,5-diamino-2-allylaminopyridine
3,5-diamino-2-(p-stilbylamino)pyridine
3,5-diamino-2-(α-pyridylamino)pyridine
3,5-diamino-2-methylamino-4,6-dimethylpyridine
2,3,5-triamino-4-ethylpyridine
2,3,5-triamino-6-methylpyridine
2,3,5-triamino-4,6-dimethylpyridine
3,4,5-triamino-2,6-dimethylpyridine
3,5-diamino-2-anilino-4,6-dimethylpyridine
3,5-diamino-4-(n-propylamino)pyridine
3,5-diamino-2,6-dimethyl-4-(methylamino)pyridine
3,5-diamino-2-(p-cyanobenzylamino)pyridine and
3,5-diamino-2-(m-R′-$C_6H_4$)pyridines in which R′ can be such monovalent radicals as $-SH$, $-CN$, $-COOH$, $-SO_3H$,

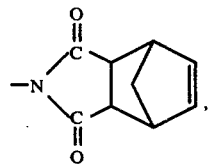

or $-SCH_3$.

In preparing the polymers of this invention triamines with reactive groups such as alkenyl, dialkylamino, cyano,

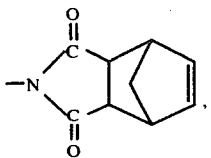

mercapto, carboxylic acid, phenylcarboxlate, and sulfonic acid are preferably used in small amounts as comonomers with other triamines of this invention. Such functional groups are desirable for increasing initial polymer solubility or for enhancing subsequent thermal crosslinking of polymer via addition or condensation reactions.

The triamines of this invention are prepared by reduction of compounds represented by the formula

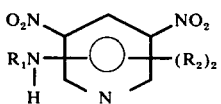

which are the 3,5-dinitro analogs of Compound I, respectively. A preferred method of reduction consists in hydrogenation using a catalyst in the presence of a strong acid selected from the group consisting of $H_3PO_4$, $H_2SO_4$, HCl, HBr, $CF_3CO_2H$, lower alkanesulfonic acids, and perfluoroalkanesulfonic acids and using a lower alcohol, polyfluorinated alcohol, or alkoxyalcohol, acetic acid or propionic acid, as cosolvent. In this manner isolation and recovery of the acid salt of the triamino compound can be readily effected by separation from the catalyst with subsequent removal of volatiles or precipitation with nonsolvent. Triamine acid salts can be used for preparing other salts or mixed acid salts by methods similar to those taught in my U.S. Pat. No. 3,740,410 issued June 19, 1973.

The triamines of this invention are generally unstable and extremely sensitive to oxidation and although they may be stored at subzero temperatures, they are preferably stored and used as their polyacid salts. Acids whose salts are suitable include: HCl, HBr, $H_2SO_4$, $H_3PO_4$, alkanesulfonic acids, $CF_3SO_3H$, and $CF_3CO_2H$. Triamines of this invention can be regenerated from their acid salts by careful neutralization under anaerobic conditions, preferably below room temperature.

The triamines as their acid salts are used to prepare precyclized polyamide precursors to thermally stable poly(amidebenzimidazoles), poly(imide-imidazopyrrolones), poly(imide-benzimidazoles), and poly(amide-imidazopyrrolones) by a process essentially identical to that described in copending U.S. Pat. application Ser. No. 151,601 filed June 9, 1971 now U.S. Pat. No. 3,804,804 granted Apr. 16, 1974 and in a copending application Ser. No. 447,638 filed Mar. 4, 1974 now abandoned and refiled as Ser. No. 617,263 on Sept. 26, 1975.

This process comprises reacting at least one triamine acid salt with at least one of the following acid derivatives: a bis(acid halide), a mono(acid halide) anhydride or a dianhydride, or mixtures thereof, in a polar aprotic solvent at temperatures ranging from about −10° C to about 75° C and preferably below about 40° C wherein the total moles of amine salt(s) is essentially equal to the total moles of acid derivative(s). The precyclized polymers can be chemically or thermally cyclodehydrated to the above cyclized polymers by known methods.

The 3,5-dinitro precursors to the triamines of this invention are prepared by one of the following methods: (a) nitration of a 2- or 4-aminopyridine or 2-alkylamino or 4-alkylamino pyridine and their ring alkylated derivatives, (b) reaction of a 2-halo- or 4-halo-3,5-dinitropyridine with a primary aliphatic, arylalkyl or aromatic amine as taught in Bull. Acad. Polon. Sci., Ser. Sci. Chim. 8 (5), 219 (1960), Roczniki Chem. 34, 465 (1960), and Roczniki Chem. 43 (11), 1961 (1969), and (c) reaction of a 2-amino-3,5-dinitropyridine, or its N-acetyl or N-carbamate derivatives, with a primary aliphatic or arylalkyl amine.

Method (a) above is unsuitable for the preparation of 3,5-dinitro precursors to compound I where $R_1$ is alkenyl or phenyl because these substituents will oxidize or nitrate under the reaction conditions necessary to produce the 3,5-dinitro-pyridine derivative. Method (c) is preferably carried out with an excess of primary aliphatic or arylalkyl amine, at temperatures between room temperature and about 190° C in primary amine as solvent or in a polar aprotic solvent such as dimethylsulfoxide, N,N-dimethylformamide, N,N-dimethylacetamide, N-methylpyrrolidinone, tetramethylenesulfone, hexamethylphosphoroamide, or mixtures thereof, or mixtures with less polar, unreactive aprotic solvents. The temperature of reaction is governed by the basicity and geometry of the amine reactant, less basic amines or sterically hindered amines requiring higher temperatures. For example, methylamine ($pk_b = 10.7$) can be reacted with 2-amino-3,5-dinitropyridine or ethyl 3,5-dinitro-2-pyridinecarbamate at room temperature to about 50° C in dimethylsulfoxide-N,N-dimethylformamide to afford excellent yields of 2-(methylamino)-3,5-dinitropyridine. Higher temperatures are required to achieve these yields using allylamine ($pk_b=9.5$) and even higher temperatures are required with the more hindered benzylamine ($pk_b=9.4$). Aromatic or heterocyclic primary amines of low basicity ($pk_b$ of about 7 or less) are unsatisfactory in this reaction.

Representative amines that are suitable for use in the process of method (c) include methylamine, n-butylamine, allylamine, crotylamine, 1,2-diaminoethane (large excess), benzylamine, β-phenylethylamine, β-(4-cyanophenyl)ethylamine, and 3-(dimethylamino)propylamine. Representative amines useful for method (b) include the above and also include aniline, p-toluidine, m-phenylenediamine (large excess), 2,6-diaminopyridine (large excess), mono-aminopyridines, 4-aminostilbene, 4-aminobiphenyl, 4-(4′-aminophenyl)pyridine, 2-aminoquinoline, the monoimide 1:1 adduct of m-phenylenediamine and endo-cis-bicyclo[2.2.1]-5-heptene-2,3-dicarboxylic anhydride, the alkali metal or quaternary ammonium salts of p-aminobenzoic or sulfanilic acids, and of p-aminothiophenol.

Many of the triamino compounds of Formula I can be prepared by either method (b) or (c) described above. However, method (c) is preferred because the 2-halo-3,5-dinitropyridine which is required for method (b) is derived from the corresponding 2-hydroxy-3,5-dinitro-derivative which can be prepared from pyridine or an alkylated pyridine in three steps, whereas the 2-amino analog used in method (c) can be prepared in only two steps from pyridine.

3,5-Dinitro precursors to compounds I where $R_1$ has labile reactive groups such as —CN, —CO$_2$C$_6$H$_5$ and

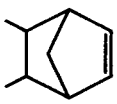

generally cannot be prepared directly from commercially available amines and are prepared from compounds containing—COOH groups by known methods.

Compounds containing the imide group

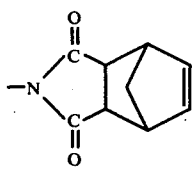

may be prepared via method (c) using the amine

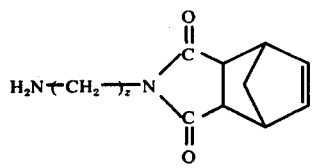

or via method (b) using the amine

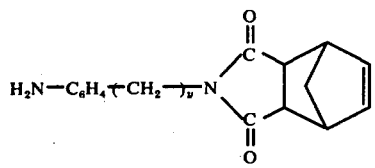

where up to one aromatic CH of C$_6$H$_4$ is replaced by nitrogen and y and z are as previously defined. Alternately the imide containing compounds may be prepared by reaction of 2-amino-4-(R$_2$)-6-(R$_2$)-3,5-dinitropyridine with a large excess of diamine

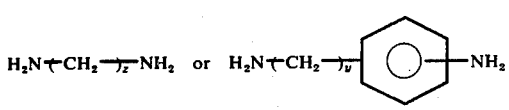

with subsequent reaction with

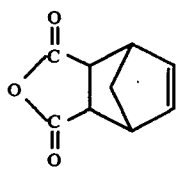

(endo-cis-bicyclo[2.2.1]-5-heptene-2,3-dicarboxylic anhydride).

The 3,5-dinitropyridine compounds used in method (c) above are prepared by nitration of the corresponding 2-aminopyridines or N-substituted derivatives thereof by methods described in the prior art, e.g., in my U.S. Pat. No. 3,740,410 issued June 19, 1973 and in my Pat. application Ser. No. 3,804,804 issued Apr. 16, 1974. The N-substituted 2-aminopyridines such as the acetamido or carbamate derivatives are prepared by methods well known in this art.

EXAMPLE 1

Preparation of 2-amino-4,6-dimethyl-3,5-dinitropyridine

To a solution of 2-amino-4,6-dimethylpyridine (122 g, 1.0 mole) in 500 ml conc. H$_2$SO$_4$ was gradually added, with good stirring, 90% HNO$_3$ (4.0 moles). The nitration mixture was kept at 10°–20° C for 2 hours; at 50° C for 2 hours; and at 85° C for 1 hour. 2-Diamino-4-methyl-3,5-dinitropyridine was isolated in 68% yield by pouring the nitration mixture onto ice, filtering product and washing well with methanol-water (1v/1v) and then water. Anal. Calcd. for C$_7$H$_8$N$_4$O$_4$: C, 39.6; H, 3.8; N, 26.4. Found: C, 39.7; H, 4.0; N, 26.2.

EXAMPLES 2–6

Following a procedure similar to that of Example 1, but substituting the amine derivative indicated below for 2-amino-4,6-dimethylpyridine the corresponding 3,5-dinitro compounds of Examples 2–6 were obtained. Anhydrous (100%) sulfuric and nitric acids were employed for Examples 5 and 6.

| Example | Amine Derivative |
|---|---|
| 2 | 4-amino-2,6-dimethylpyridine |
| 3 | 2-amino-6-ethylpyridine |
| 4 | 2-amino-4-n-propylpyridine |
| 5 | ethyl 4-methyl-2-pyridine carbamate |
| 6 | 2-acetamido-6-methylpyridine |

EXAMPLE 7

Preparation of 2-(methylamino)-6-methyl-3,5-dinitropyridine

To a solution of 2-amino-6-methyl-3,5-dinitropyridine (24.9 g, 0.125 mole) and 175 ml dimethylsulfoxide in a 500 ml Parr bottle was added a solution of methylamine (20 g, 0.65 mole) in 75 ml N, N-dimethylacetamide. The reaction was shaken for 6 hours at ambient temperature and then heated 15 hours at 70° C. Upon cooling, the mixture was diluted with water, filtered, washed with methanol-water (1v/1v) and dried. 2-(methylamino)-6-methyl-3,5-dinitropyridine was obtained as a yellow solid (82% yield). Anal. Calcd. for C$_7$H$_8$N$_4$O$_4$: C, 39.6; H, 3.8; N, 26.4. Found: C, 39.6; H, 3.9; N, 26.3.

EXAMPLES 8–16

Following a procedure similar to that described for Example 7, but substituting for the 2-amino-6-methyl-3,5-dinitropyridine and methylamine, respectively, the dinitro compound represented by the formula and amine (RNH$_2$) indicated below, the following 3,5-dinitropyridine derivatives of Examples 8–16 were obtained where the—NH$_2$ (or substituted—NH$_2$) group of starting material is replaced by the RNH- group of the amine.

| Ex. | Dinitro Starting Material | | | Amine Coreactant | Reaction Conditions | |
|---|---|---|---|---|---|---|
| | $R_a$ | $R_b$ | $R_c$ | $RNH_2$, R = | °C | Hrs. |
| 8* | $NH_2$ | H | $CH_3$ | $n\text{-}C_4H_9\text{—}$ | 70 | 20 |
| 9 | $CH_3$ | $NH_2$ | $CH_3$ | $n\text{-}C_3H_9\text{—}$ | 70 – 80 | 20 |
| 10 | $NH_2$ | H | H | $CH_2\text{=}CH\text{—}CH_2\text{—}$ | 90 – 100 | 15 |
| 11 | $CH_3CNH$ (O=) | H | $CH_3$ | $CH_3CH\text{—}CH\text{—}CH_2\text{—}$ (1.0 mole) | 70 / 90 – 100 | 20 / 10 |
| 12 | $NH_2$ | $CH_3$ | $CH_3$ | $(CH_3)_2NC_3H_6\text{—}$ | 25 / 50 | 5 / 20 |
| 13 | $NH_2$ | $n\text{-}C_3H_4$ | H | $p\text{-}CNC_6H_4CH_2CH_2\text{—}$ | 50 / 80 – 90 | 10 / 24 |
| 14 | H | $NH_2$ | H | $H_2NCH_2CH_2\text{—}$ (500% excess) | 25 / 50 – 60 | 5 / 10 |
| 15 | $C_2H_5OCNH$ (O=) | $CH_3$ | H | $2\text{-}C_5H_4NCH_2\text{—}$ (2-pyridyl amine;1.0 mole) | 70 / 90 | 10 / 20 |
| 16 | $NH_2$ | H | $C_2H_5$ | $C_6H_5CH_2\text{—}$ | 70 / 90 – 100 | 20 / 20 |

*This product was also obtained by nitration of 2-(n-butylamino)-6-methylpyridine.

EXAMPLE 17

Preparation of 2-(α-pyridylamino)-3,5-dinitropyridine

A mixture of 2-chloro-3,5-dinitropyridine (20.4 g, 0.10 mole) 15 ml absolute ethanol, potassium bicarbonate (11.0 g, 0.11 mole), and 2-aminopyridine (28.2 g, 0.30 mole) was refluxed for 24 hours. The mixture was concentrated to one-half of its volume and diluted with several volumes of water to precipitate solid. After further washing and drying 2-(α-pyridylamino)-3,5-dinitropyridine (81% yield) was obtained as a golden, yellow solid. Anal. Calcd. for $C_{10}H_7N_5O_4$: C, 46.0; H, 2.7; N, 26.8 Found: C, 46.1; H, 2.9; N, 27.0

EXAMPLES 18–25

Following a procedure similar to that described for Example 17 using 1–3 days reflux time and 10% HCl to precipitate product, but substituting for the 2-chloro-3,5-dinitropyridine and 2-aminopyridine respectively, the dinitro compound represented by the formula

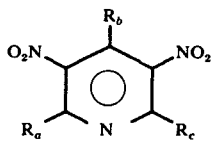

and amine ($RNH_2$) indicated below, the following 3,5dinitropyridine derivatives of Examples 18–25 were obtained where the Cl or Br group of starting material is replaced by the RNH- group of the amine.

| Ex. | Dinitro Starting Material | | | Amine Coreactant $RNH_2$, R = |
|---|---|---|---|---|
| | $R_a$ | $R_b$ | $R_c$ | |
| 18* | Cl | H | $CH_3$ | $C_9H_6N\text{—}$ (2-quinolyl) |
| 19 | $CH_3$ | Cl | $CH_3$ | $p\text{-}C_6H_5C_6H_4\text{—}$ |
| 20 | Cl | H | $C_2H_5$ | $m\text{-}ClC_6H_4\text{—}$ |
| 21 | Cl | H | H | $p\text{-}C_6H_5CH\text{=}CHC_6H_4\text{—}$ |
| 22 | Cl | $CH_3$ | $CH_3$ | $p\text{-}C_2H_5C_6H_4\text{—}$ |
| 23 | Br | H | H | 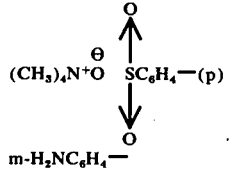 |
| 24* | Cl | H | H | $m\text{-}H_2NC_6H_4\text{—}$ |
| 25 | Cl | $CH_3$ | H | (500% excess) $p\text{-}HSC_6H_4\text{—}$ |

*Water, not 10% HCl was used to precipitate product.

EXAMPLE 26

Preparation of 2,3,5-triamino-4,6-dimethylpyridine and Acid Salts

A. Hydrochloride Salt and Free Triamine

A 500 ml Parr Bottle was charged with 2-amino-4,6-dimethyl-3,5-dinitropyridine (21.2 g, 0.10 mole), 250 ml absolute ethanol, and 20 g 5% Pd/charcoal catalyst. The mixture was subjected to hydrogenation at ambient temperature with an initial hydrogen pressure of 60 psig. When no further uptake of hydrogen was observed, the mixture was filtered free of catalyst under a nitrogen atmosphere, and concentrated under vacuum to a volume of about 100 ml. The product concentrate was treated, under nitrogen at ice temperature, with a cold solution of hydrogen chloride (0.5 mole) in 85 ml anhydrous isopropyl alcohol. The trihydrochloride salt of 2,3,5-triamino-4,6-dimethylpyridine was obtained after vigorous stirring, filtering under nitrogen, and vacuum drying under high vacuum over $P_2O_5$ at 80°–90° C.

The free triamine base was obtained either by concentration and drying prior to addition of HCl as described above or by suspending the hydrochloride salt in absolute deoxygenated isopropyl alcohol, neutralizing with a concentrated methanolic solution of potassium methoxide under nitrogen, filtering off KCl, and removal of solvents from the filtrate. Anal. Calcd. for $C_7H_{12}N_4$: C, 55.3; H, 7.9; N, 36.8. Found: C, 55.1; H, 8.0; N, 36.7.

Purified 2,3,5-triamino-4,6-dimethylpyridine could be used to prepare the other acid salts of Example 26 as well as the acid salts derived from HBr, $H_3PO_4$ and $H_2SO_4$.

B. Methanesulfonate Salt

A 500 ml Parr Bottle was charged with 2-amino-4,6-dimethyl-3,5-dinitropyridine (21.2 g, 0.10 mole), 200 ml methanol, methanesulfonic acid (19.2 g, 0.20 mole), and 20.g 5% Pd/charcoal catalyst. The mixture was subjected to hydrogenation at ambient temperature with an initial hydrogen pressure of 5.7 psig. When no further uptake of hydrogen was observed, the mixture was filtered free of catalyst under a nitrogen atmosphere, and methanol removed under vacuum. The bismethanesulfonate salt of 2,3,5-triamino-4,6-dimethylpyridine so obtained was purified by slurrying with dry isopropyl alcohol, filtering under nitrogen, and vacuum drying over $P_2O_5$ at 80°–90° C.

C. Trifluoroacetate Salt

The procedure of Example 26 B was followed except that $CF_3CO_2H$ (0.20 mole) was substituted for the methanesulfonic acid. The bistrifluoroacetate salt was obtained directly after complete removal of solvent under high vacuum.

D. Trifluoromethanesulfonate Salt

The procedure of Example 26 B was followed except that $CF_3SO_3H$ (0.10 mole) was substituted for the methanesulfonic acid. The monotrifluoromethanesulfonate salt was obtained directly after complete removal of solvent under high vacuum.

EXAMPLES 27–35

The polyamino acid salts of Examples 27–35 were prepared by using the dinitro intermediates indicated below and following the reduction procedures of Example 26.

(7.67 g, 0.025 mole) was added over five minutes under a nitrogen atmosphere to a stirred cold mixture of 2,3,5-triaminopyridine trihydrochloride (5.84 g, 0.025 mole) and 45 g N-methylpyrrolidinone. The reaction was maintained at 0°–5° C for two hours and then kept at room temperature for 4 hours. The polymer solution was poured into 175 ml methanol with stirring. The resulting precipitate of precyclized polymer was filtered, washed well with methanol twice and vacuum dried overnight at 50°–55° C. The hydrochloride polymer (9.1 g) was obtained as a yellow powder which was soluble in N,N-dimethylformamide (DMF), dimethylsulfoxide (DMSO), and formic acid and had an inherent viscosity of 0.5 dl/g in DMF (0.5% conc., 30° C). A strongly positive Beilstein test confirmed in the presence of chloride.

This polymer was neutralized as follows: the hydrochloride polymer (3.0 g) was dissolved in DMF (25 ml), treated with triethylamine (1 ml) and then precipitated by pouring into methanol, with stirring. The neutral polymer precipitate was purified in the same manner as the hydrochloride polymer precipitate. The neutral precyclized polymer was soluble in DMF, DMSO and formic acid. Anal. Calcd. for $C_{20}H_{14}N_4C_3$: C, 67.0; H, 3.9; N, 15.7.

The precyclized hydrochloride polymer was converted to the cyclized polymer by heating two hours

| Ex. | Dinitro Starting Material | Polyamine Isolated as a Polysalt of |
|---|---|---|
| 27 | 2-(n-butylamino)-6-methyl-3,5-dinitropyridine | HBr |
| 28 | 4-amino-2,6-dimethyl-3,5-dinitropyridine | HCl |
| 29 | 2-benzylamino-6-ethyl-3,5-dinitropyridine | $CF_3SO_3H$ |
| 30 | 2-(β-pyridylamino)-3,5-dinitropyridine | HCl |
| 31 | 2-(p-stilbylamino)-3,5-dinitropyridine | HCl |
| 32 | 2-(p-sulfoanilino-3,5-dinitropyridine | $CH_3SO_3H$ |
| 33[b] | 2-(allylamino)-3,5-dinitropyridine | $CF_3COOH$ |
| 34 | 2-(p-mercaptoanilino)-4-methyl-3,5-dinitropyridine | HCl |
| 35[c] | 2-(R)-3,5-dinitropyridine where R = | HCl |

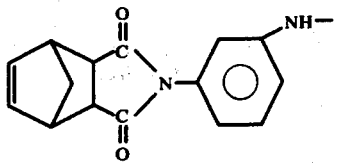

[a] Each nitro group of starting material is replaced by a $-NH_2$ group.
[b] The procedure of Example 26 C was followed except that the $CF_3CO_2H$ (3.3 equiv/mole of dinitro intermediate) was added after filtration of catalyst.
[c] The dinitro starting material was prepared by reaction of the product of Example 24 with endo-cis-bicyclo-[2.2.1]-5-heptene-2,3-dicarboxylic anhydride followed by imide formation in the resulting adduct.

EXAMPLE 36

Precyclized Polymer and Poly(amide-benzimidazole) from 2,3,5-Triaminopyridine Trihydrochloride and 4,4'-Carbonyldibenzoyl Chloride 4,4'-Carbonyldibenzoyl chloride

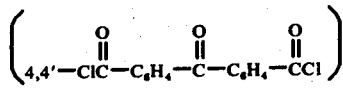

under vacuum at each of the following temperatures, 150°, 200°, 300°, and 350° C. The resulting poly(amide-benzimidazole) was soluble in formic trifluoroacetic, sulfuric and methanesulfonic acid. Anal. Calcd. for $C_{20}H_{10}N_4O$: C, 74.5; H, 3.1; N, 17.4. Found: C, 73.8; H, 3.3; N, 17.2.

Other acid salts of the above precyclized polymer may be formed by replacing the trihydrochloride salt by either the hydrobromide or the methanesulfonate. The salts could be converted to cyclized polymer in the same way.

EXAMPLE 37

Precyclized Polymer and Poly(Imide-Imidazopyrrolone) from 2,3,5-Triaminopyridine Trihydrochloride and 3,3',4,4'-Benzophenonetetracarboxylic Dianhydride The procedure of Example 36 was followed except that 3,3',4,4'-benzophenonetetracarboxylic dianhydride (0.025 Mole) was substituted for the 4,4'-carbonyldibenzoyl chloride, and the reaction was conducted 2 hours at 5°–10° C and 17 hours at room temperature. An essentially quantitative yield of precyclized hydrochloride polymer was obtained which was soluble in DMF, DMSO, and $H_2SO_4$. The chloride-free precyclized polymer was obtained by neutralization of the HCl in a manner similar to that described in Example 36. Anal. Calcd. for $C_{22}H_{14}N_4O_7$: C, 59.2; H, 3.1; N, 12.6. Found: C, 59.0; H, 3.4; N, 12.5.

The precyclized polymer above was cyclodehydrated to poly(imide-imidazopyrrolone) by heating under vacuum as described in Example 36. The cyclized polymer retained 97% of its original weight after 100 hours exposure to air at 600° F (316° C).

The preceding examples are not intended to limit the invention in any way, but are merely exemplary of preferred embodiments of the invention.

Particularly preferred triaminopyridines within the scope of this invention are those represented by the formula:

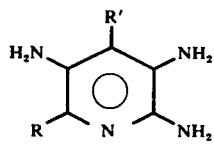

in which one of R and R' is —$CH_3$ and the other is either —H or —$CH_3$.

The above described novel triamino pyridine compounds were reacted with bis(acid halides) in the same manner as described in my U.S. Pat. No. 3,783,137 issued Jan. 1, 1974 and in my U.S. Pat. application Ser. No. 151,601 filed June 9, 1971, and in an article published in Journal of Polymer Chemistry, Chem., Ed. 11, 1703 (1973).

Bis(acid halides) which have been reacted with the triamino monomers of the present invention are those generally represented by the formula

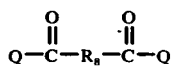

in which each Q is halogen selected from the group consisting of F, Cl and Br; and $R_8$ is a divalent paraffinic, perfluoroalkyl, perfluoropolyalkylene oxide, alkenyl, aromatic or inorganic/organic radical including acylic paraffinic, cycloparaffinic, carbocyclic radicals and heterocyclic radicals having a single, multiple or fused ring structure, the multiple ring structures including polyarylenes with 2 to 9 aryl rings in which the aryl groups are bonded directly to each other or bridged by a divalent member selected from the group consisting of alkylene with up to 3 carbon atoms,

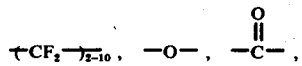

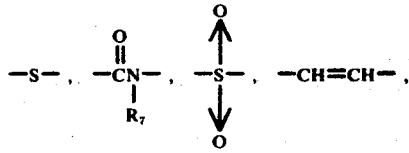

5- and 6-membered heteroaromatics containing at least one nitrogen atom and mixtures thereof, and substituted aromatic radicals where the substituents are selected from lower alkyl, F, Cl, —CN, —$SO_3H$, and

the inorganic/organic radicals consisting of ferrocenyl, carboranyl, and biaryls separated by at least one phosphorus atom or by at least one silanyl or siloxanyl group, and mixtures thereof; and $R_7$ represents H, lower alkyl or phenyl.

It is also possible to replace some or all of the bis(acid halides) with mono(acid halide) anhydrides or dianhydrides.

Suitable mono- or di-anhydrides are useful as comonomers for reactions with the triamino compounds of this invention, particularly when $R_1$ of Formula I is hydrogen Suitable acid derivatives are those which have similar generic compositions to those described for $R_8$ above.

I claim:

1. Substituted 3,5-dinitropyridines represented by the formula:

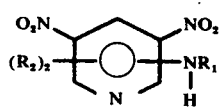

wherein each $R_2$ is a monovalent member selected from the group consisting of H and methyl and $R_1$ represents a monovalent member represented by the formula —$(CH_2)_nC_6H_4X$ wherein n is an integer selected from the group consisting of 0, 1 and 2 and X is a meta- or para-substituent selected from the group consisting of —CN, —$SO_3H$, —SH, —thioalkyl, —thioaryl, —CH=$CHC_6H_5$, and

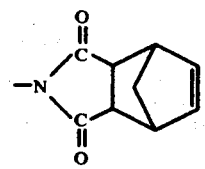

2. A process for the preparation of 3,5-dinitropyridine compounds which comprises:

1. reacting a 3,5-dinitropyridine compound represented by the formula

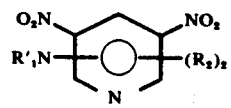

wherein $R'_1$ is a monovalent member selected from the group consisting of H,

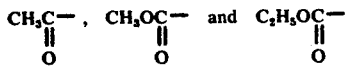

and each $R_2$ is a monovalent member selected from the group consisting of H and alkyl and both $R_2$'s are not required to be the same; with 2. a primary amine represented by the formula $R'NH_2$ wherein $R'$ is a monovalent radical selected from the group consisting of $C_1$-$C_4$ alkyl; substituted $C_1$-$C_4$ alkyl, wherein the substituents are selected from the group consisting of —CN, COOH salts, $SO_3H$ salts, —SH, -thioalkyl, -thioaryl, —CH=CHC$_6$H$_5$, —NH$_2$, —N(CH$_3$)$_2$; arylalkyl and substituted arylalkyl represented by the formula —(CH$_2$)—$_m$ C$_6$H$_4$Y wherein Y is a meta or para substituent selected from the group consisting of —NH$_2$, —CN, —SO$_3$H, —SH, -thioalkyl, -thioaryl, —CH=CHC$_6$H$_5$ and,

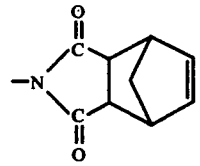

—(CH$_2$)—$_m$ pyridyl wherein $m$ is an integer selected from the group consisting of 1 and 2; and $C_3$-$C_4$ alkenyl;

said reaction being effected at a temperature of between about 25° C and 100° C and in a solvent selected from the group consisting of polar aprotic solvents, primary amine, $R'NH_2$, and mixtures thereof.

3. The compound of claim 1 wherein both $R_2$'s and H and $R_1$ is

* * * * *